United States Patent [19]

Kato et al.

[11] 4,439,866
[45] Mar. 27, 1984

[54] ARBITRARY LAYER TOMOGRAPHIC METHOD AND APPARATUS

[75] Inventors: Hisatoyo Kato; Masamitsu Ishida, both of Kanagawa, Japan

[73] Assignee: Fuji Photo Film Co., Ltd., Kanagawa, Japan

[21] Appl. No.: 511,074

[22] Filed: Jul. 5, 1983

[30] Foreign Application Priority Data

Jul. 19, 1982 [JP] Japan ................................ 57-125475

[51] Int. Cl.$^3$ ............................................. G03B 41/16
[52] U.S. Cl. .................................. 378/19; 250/327.2; 378/4
[58] Field of Search .................... 378/4, 19; 250/327.2

[56] References Cited

U.S. PATENT DOCUMENTS 3,975,637 8/1976 Ikedo ............................... 250/327.2
4,164,657 8/1979 Duinker ................................ 378/19

Primary Examiner—Craig E. Church
Attorney, Agent, or Firm—Sughrue, Mion, Zinn, Macpeak, and Seas

[57] ABSTRACT

Many two-dimensional X-ray projection distribution images obtained by exposing an object to X-rays in various directions are once stored in positions different from one another in a stimulable phosphor sheet or respectively in many stimulable phosphor sheets. The stimulable phosphor sheet or sheets are then scanned with stimulating rays, and the light emitted thereby from the stimulable phosphor sheet or sheets is photoelectrically read out to obtain electric signals representing the X-ray projection distribution images. The electric signals are processed to obtain a tomographic image of an arbitrary tomographic layer of the object.

10 Claims, 6 Drawing Figures

ARBITRARY LAYER TOMOGRAPHIC METHOD AND APPARATUS

BACKGROUND OF THE INVENTION

1. Field of the Invention

This invention relates to an arbitrary layer tomographic method and an apparatus for carrying out the method. This invention particularly relates to an arbitrary layer tomographic method using at least one stimulable phosphor sheet, and an apparatus for carrying out the method.

2. Description of the Prior Art

In the computed tomographic apparatus (hereinafter referred to as a CT scanner) developed by Hounsfield et al., a tomographic image of a predetermined tomographic layer of an object is composed from a plurality of X-ray projection disctribution images obtained by exposing the tomographic layer of the object to X-rays in many different directions. As the CT scanner can provide a sharp tomographic image of a soft tissue, which could not be obtained with the convenitonal method using X-ray films, it has attracted much attention in the field of medical diagnosis.

Since the aforesaid CT scanner is intended to obtain a tomographic image of a predetermined tomographic layer of an object, it is impossible to obtain three-dimensional information over a wide range of a structure (e.g. an organ, bone, blood vessel, or the like) of the object by a single image recording operation using the CT scanner. In order to obtain three-dimensional information over a wide range of a structure of the object by use of the CT scanner, the image recording operation must be conducted several times for tomographic layers different from one another. However, when the image recording operation is conducted several times for the same object, the time required for the image recording becomes long. Further, deviations in position of the structure to be diagnosed occur among the tomographic images obtained by the respective image recording operations due to muscular motion, breathing motion, vermicular motion, or the like during the prolonged image recording time. As a result, it is not always possible to correctly diagnose the structure from the tomographic images.

As described in Math. Phys. KI. 69, pp. 262 to 277 (1917) by J. Radon, it has been mathematically verified that a two-dimensional object or a three-dimensional object can be unitarily reproduced from an infinite number of sets of projection data of the object. In the aforesaid CT scanner, a two-dimensional image is reproduced from one-dimensional projection image signals of a two-dimensional object obtained at various angles with respect to the object. Theoretically, however, it will also be possible to reproduce a three-dimensional image from two-dimensional projection image signals of a three-dimensional object obtained at various angles with respect to the object. This is called "three-dimensional reconstruction from radiographs" and there are a lot of technical reports thereabout. If a technique of reproducing a three-dimensional object from two-dimensional projection image signals of the object is developed, the technique will be very advantageous for medical diagnosis since it will become possible to obtain a tomographic image (two-dimensional image) of an arbitrary layer of a structure of the object by a single image recording operation.

However, in order to use the detector of the CT scanner as a two-dimensional sensor for obtaining a tomographic image of an arbitrary tomographic layer of a structure of an object, a very large number of detection elements must be positioned two-dimensionally. It takes a very long time for image signals to be transferred from the two-dimensional sensor comprising many detection elements and, consequently, the time required for the image recording becomes long. An increase in the image recording time presents a very serious problem in a method of composing an image having a given number of dimensions from a plurality of projection image signals having dimensions lower by one dimension than the dimensions of the image. Namely, when a stationary image of the head, the skeleton, or the like is recorded, no serious problem is presented even if the image recording time is prolonged. However, when an image of an organ is recorded, the condition of the organ changes due to muscular motion, breathing motion, vermicular motion, or the like during the prolonged image recording time. As a result, the contrast and the spatial resolution of the tomographic image ultimately obtained are adversely affected, or noise called artifact occurs, making it impossible to obtain a tomographic image suitable for viewing and diagnostic purposes. When the detector, which is employed in the CT scanner, is used as the two-dimensional sensor, the time required for the image recording becomes too long to obtain an image suitable for viewing and diagnostic purposes. Therefore, there has not heretofore been any practicable apparatus for obtaining image information representing a three-dimensional image of an object, thereby obtaining a tomographic image of an arbitrary tomographic layer of the object.

In general (also in the conventional CT scanner), in order to achieve high diagnostic accuracy and efficiency, the tomographic image should exhibit a spatial resolution sufficient to permit discrimination of details of the tissue. The spatial resolution of the tomographic image ultimately obtained depends on the number of detection elements of the detector per unit space. However, when detection elements employed in the CT scanner (for example photomultipliers provided with scintillators on light receiving faces) are used as the detection elements, a sufficient spatial resolution cannot be obtained because such photomultipliers have a large size and the number thereof per unit space of the detector becomes small. High-pressure xenon gas detection elements and semiconductor detection elements can be positioned more densely than photomultipliers. In this case, however, the spatial resolution that can be realized is at most about 1 line/mm. Furthermore, high-pressure xenon gas and semiconductor detection elements exhibit a lower sensitivity than photomultipliers provided with scintillators on light receiving faces. Therefore, to obtain a tomographic image of the same quality as when photomultipliers are used, it is necessary to increase the radiation dose which the object receives. Further, when the detector is composed of a plurality of detection elements, the respective detection elements should exhibit the same sensitivity. However, from the technical viewpoint, it is not always possible to make the detection elements exhibit exactly the same sensitivity.

SUMMARY OF THE INVENTION

The primary object of the present invention is to provide an arbitrary layer tomographic method which can compose a tomographic image of an arbitrary tomographic layer of an object as an image having an improved image quality, particularly a high diagnostic efficiency and accuracy.

Another object of the present invention is to provide an arbitrary layer tomographic method wherein image recording can be conducted very quickly and at a high sensitivity.

The specific object of the present invention is to provide an apparatus for carrying out the arbitrary layer tomographic method.

The arbitrary layer tomographic method in accordance with the present invention comprises once storing a plurality of two-dimensional X-ray projection distribution images, which are obtained by exposing an object to X-rays in a plurality of different directions, in positions different from one another in a single stimulable phosphor sheet or respectively in a plurality of stimulable phosphor sheets, scanning said stimulable phosphor sheet or sheets with stimulating rays, photoelectrically reading out the light emitted thereby from said stimulable phosphor sheet or sheets and obtaining electric signals representing the image information of a plurality of said X-ray projection distribution images, processing said electric signals and obtaining the image information representing a tomographic image of an arbitrary tomographic layer of said object.

The arbitrary layer tomographic apparatus in accordance with the present invention comprises an X-ray source capable of emitting X-rays in a plurality of different directions with respect to an object, at least one stimulable phosphor sheet for receiving the X-rays passing through said object and storing therein two-dimensional X-ray projection distribution images in a plurality of different directions, a scanning means for two-dimensionally scanning said stimulable phosphor sheet with stimulating rays, a photoelectric converting means for photoelectrically reading out the light emitted from said stimulable phosphor sheet by said scanning with stimulating rays and obtaining image signals, and a signal processing means for composing a tomographic image of an arbitrary tomographic layer of said object from said image signals.

In the present invention, the stimulable phosphor sheet is provided with a layer of a stimulable phosphor exhibiting the properties described below. Namely, when the stimulable phosphor is exposed to a radiation such as X-rays, α-rays, β-rays, γ-rays or ultraviolet rays, it absorbs and stores a part of the energy of the radiation. Then, when the stimulable phosphor which has been exposed to the radiation is exposed to stimulating rays such as visible light, light is emitted from the stimulable phosphor in proportion to the stored energy of the radiation.

The Applicant has proposed a radiation image recording and reproducing system using the stimulable phosphor, for example, in his U.S. Pat. No. 4,258,264 and Japanese Unexamined Patent Publication No. 56(1981)-11395. In this method, the stimulable phosphor sheet is first exposed to a radiation passing through an object to have a radiation image stored therein, and is then scanned with stimulating rays such as laser beam which causes the stimulable phosphor sheet to emit light in proportion to the radiation energy stored therein. The light emitted from the stimulable phosphor sheet upon stimulation thereof is photoelectrically detected and converted to an electric signal, which is processed as desired to reproduce a visible image on a recording material such as a photographic light-sensitive material or on a display device such as cathode ray tube (CRT).

In the radiation image recording and reproducing method described above, the stimulable phosphor develops electrons or positive holes therein in a number proportional to the intensity of the X-rays passing through the object. The electrons or the positive holes are trapped on the trap level of the stimulable phosphor, thereby storing the X-ray transmission image of the object as the radiation image information in the stimulable phosphor. Thereafter, when the stimulable phosphor is exposed to stimulating rays, the electrons or the positive holes trapped on the trap level are expelled to emit light upon stimulation. It is known that the intensity of light emitted from the stimulable phosphor upon stimulation thereof is proportional to the number of the electrons or the positive holes trapped therein, i.e. the intensity of the X-rays passing through the object. Accordingly, the X-ray transmission image can be obtained at a high sensitivity as an electric signal by efficiently collecting the light emitted from the stimulable phosphor upon stimulation thereof and photoelectrically converting the collected light by use of a high-sensitivity photodetector such as a photomultiplier. It is also known that the stimulable phosphor can exhibit a high spatial resolution, for example 10 lines/mm or more.

In the present invention, since X-ray projection distribution images are once recorded in at least one stimulable phosphor sheet, it is not necessary to use a detector consisting of many detection elements. Accordingly, the time required for transferring the image signals when the two-dimensional sensor consisting of many detection elements is used can be made zero at the time of recording the X-ray image, and the image recording time is reduced extremely. Further, since the stimulable phosphor sheet is used, the image recording can be conducted at a high spatial resolution and at a high sensitivity, and the risk of a problem with regard to fluctuation in sensitivity occurring among the detection elements is eliminated. Accordingly, it is possible to obtain a tomographic image of an arbitrary layer of the object as a reproduced image having an improved image quality, particularly a high diagnostic efficiency and accuracy. This is very advantageous for medical diagnosis.

In the present invention, in order to improve the signal-to-noise ratio, it is preferable for the stimulable phosphor to emit light having a wavelength range not overlapping upon the wavelength range of the stimulating ray employed to excite the stimulable phosphor. Preferably, when a laser source which emits stimulating ray having a wavelength within the range between 600 nm and 700 nm, such as a He-Ne laser, is used, a stimulable phosphor which emits light having a wavelength within the range between 300 nm and 500 nm should be selected, as disclosed in U.S. Pat. No. 4,258,264.

Further, in order to increase the amount of light read out from the stimulable phosphor and shorten the readout time, it is preferable to use a gas ion laser source emitting a laser beam having a wavelength range shorter than 600 nm, such as an $Ar^+$ laser beam (488 nm, 514.5 nm), a $Kr^+$ laser beam (520.9 nm, 530.9 nm, 568.2 nm), or an $Ar^+$-$Kr^+$ laser beam.

As the stimulable phosphor, for example, rare earth activated alkaline earth metal fluorohalide phosphor is preferred. One example of this phosphor is, as shown in DE-OS No. 2,928,245, a phosphor represented by the formula $(Ba_{1-x-y},Mg_x,Ca_y)FX:aEu^{2+}$ wherein X is at least one of Cl and Br, x and y are numbers satisfying $0 < x+y \leq 0.6$ and $xy-0$, and a is a number satisfying $10^{-6} < a \leq 5\times10^{-2}$. Another example of this phosphor is, as shown in U.S. Pat. No. 4,239,968, a phosphor represented by the formula $(Ba_{1-x},M^{II}_x)FX:yA$ wherein $M^{II}$ is at least one of Mg, Ca, Sr, Zn and Cd, X is at least one of Cl, Br and I, A is at least one of Eu, Tb, Ce, Tm, Dy, Pr, Ho, Nd, Yb and Er, x is a number satisfying $0 \leq x \leq 0.6$, and y is a number satisfying $0 \leq y \leq 0.2$. Further, as the stimulable phosphor to be used in this invention can be used ZnS:Cu,Pb; $BaO.xAl_2O_3$:Eu wherein $0.8 \leq x \leq 10$; and $M^{II}O.xSiO_2$:A wherein $M^{II}$ is Mg, Ca, Sr, Zn, Cd or Ba, A is Ce, Tb, Eu, Tm, Pb, Tl, Bi or Mn, and x is number satisfying $0.5 \leq x < 2.5$, as shown in U.S. Pat. No. 4,236,078. Furthermore, as the stimulable phosphor can be used LnOX:xA wherein Ln is at least one of La, Y, Gd and Lu, X is at least one of Cl and Br, A is at least one of Ce and Tb, x is a number satisfying $0 < x < 0.1$, as shown in U.S. Pat. No. 4,236,078. Among the above enumerated phosphors, the rare earth activated alkaline earth metal fluorohalide phosphors are the most preferable, among which barium fluorohalides are the most preferable in view of the high intensity of emission of light.

Further, barium fluorohalide phosphors added with a metal fluoride as disclosed in Japanese Unexamined Patent publication Nos. 56(1981)-2385 and 56(1981)-2386, or barium fluorohalide phosphors containing at least one of a metal chloride, a metal bromide and a metal iodide as disclosed in European Patent publication No. 29,963 are also preferable because of their improved light emitting characteristics.

It is also desirable to color the phosphor layer of the stimulable phosphor sheet made of the above phosphor by use of pigments or dyes to improve the sharpness of the image obtained thereby as disclosed in European Patent publication No. 21,174.

DESCRIPTION OF THE PREFERRED EMBODIMENTS

The present invention will hereinbelow be described in further detail with reference to the accompanying drawings.

Figure 1:
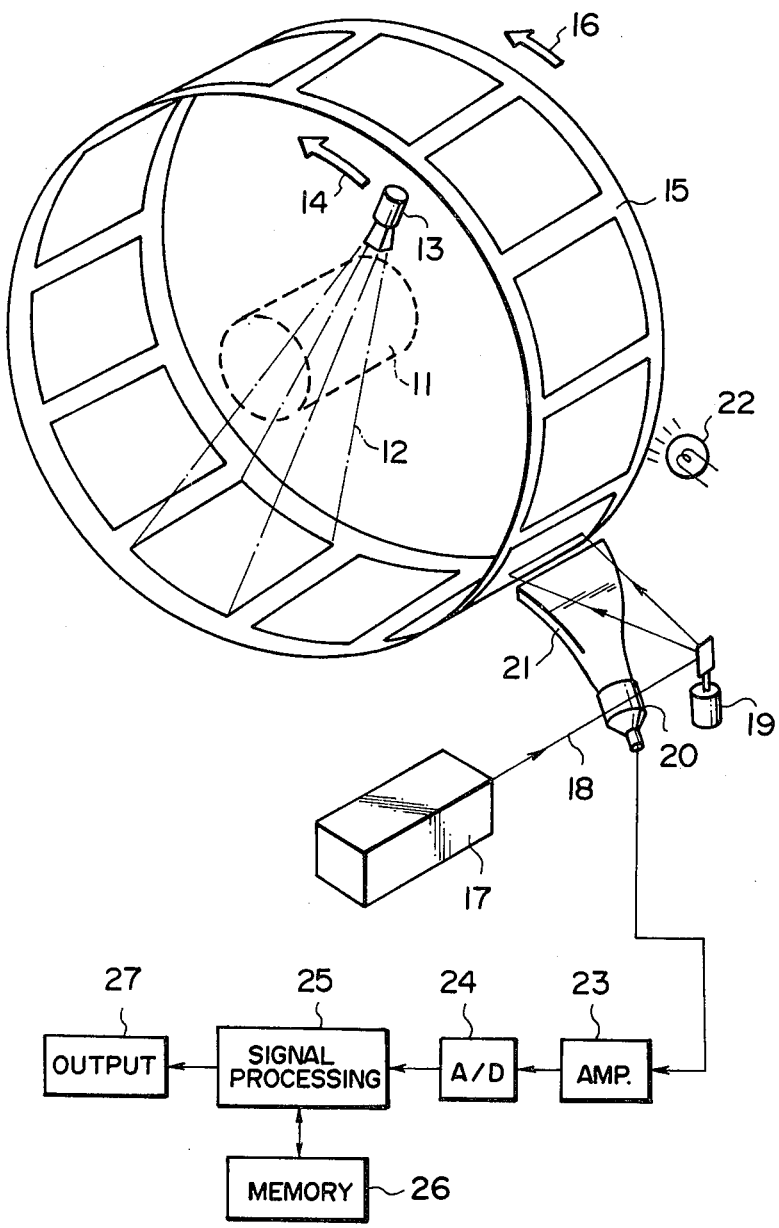
FIG. 1 is a schematic view showing a first embodiment of the apparatus in accordance with the present invention.

Referring to FIG. 1 showing a first embodiment of the apparatus in accordance with the present invention, an X-ray tube 13 for emitting a quardrangular pyramid-like X-ray beam 12 including an image recording region 11 wherein an object is positioned is installed for rotation in the direction indicated by the arrow 14 around the image recording region 11. A stimulable phosphor sheet 15 for storing therein the X-rays 12 passing through the object as two-dimensional X-ray projection distribution images is formed cylindrically and positioned around the image recording region 11 at equal distances from the center axis of the image recording region 11. The stimulable phosphor sheet 15 can be rotated in the direction indicated by the arrow 16. In the vicinity of the peripheral surface of the stimulable phosphor sheet 15 are positioned an optical scanning system for scanning the stimulable phosphor sheet 15 with stimulating rays and a light detecting means for photoelectrically detecting the light emitted from the stimulable phosphor sheet 15 when it is scanned with the stimulating rays. Specifically, there are positioned a laser source 17 for emitting a laser beam 18 having a wavelength within the stimulation wavelength range of the stimulable phosphor sheet 15, a light deflector 19 for deflecting the laser beam 18 emitted from the laser source 17 in the width direction of the stimulable phosphor sheet 15, a photodetector 20 for photoelectrically detecting the light emitted from the stimulable phosphor sheet 15 when it is stimulated by the laser beam 18, and a light transfer means 21 for efficiently transferring the light emitted from the stimulable phosphor sheet 15 to the photodetector 20. The light transfer means 21 may be of a material and a construction as disclosed in U.S. Pat. No. 4,346,295, U.S. Pat. application Ser. Nos. 105,240 and 168,805, or Japanese Unexamined Patent publication No. 56(1981)-11395, and may be used by the methods disclosed therein. An erasing light source 22 is positioned downstream of the portion where the stimulable phosphor sheet 15 is scanned with the laser beam 18 emitted from the laser source 17 (downstream with respect to the rotating direction of the stimulable phosphor sheet 15). The erasing light source 22 emits light having a wavelength within the stimulation wavelength range of the stimulable phosphor sheet 15. The light emitted from the erasing light source 22 is directed onto the stimulable phosphor sheet 15 to release the radiation energy remaining therein after the read-out step. The erasing light source 22 may, for example, be a tungsten-filament lamp, a halogen lamp, an infrared lamp, or a laser source as described in Japanese Unexamined Patent publication No. 56(1981)-11392. Since the radiation energy stored in the stimulable phosphor sheet 15 can also be eliminated by heating the stimulable phosphor sheet 15 as disclosed, for example, in Japanese Unexamined Patent publication No. 56(1981)-12599, the erasing light source 22 may be replaced by a heating means.

In FIG. 1, image recording is conducted as follows. The X-ray tube 13 is positioned at an angle with respect to the object, and X-rays 12 are emitted pulse-wise from the X-ray tube 13. The X-rays 12 passing through the object are stored in the stimulable phosphor sheet 15 as a two-dimensional X-ray projection distribution image. After the image recording is finished at one angle with respect to the object, the X-ray tube 13 is rotated by a predetermined angle with respect to the object. The image recording is again conducted as described above to obtain another X-ray projection distribution image, which is then stored in the stimulable phosphor sheet 15 so as not to overlap the previously stored X-ray projection distribution image. The image recording described above is repeated to obtain X-ray projection distribution images at equal angular intervals with respect to the object. In this manner, the image recording for obtaining a three-dimensional image of the object or an arbitrary tomographic image of the object is finished when the X-ray tube 13 has been rotated one turn (360°) around the object. After the image recording is over, the X-ray projection distribution images stored in the stimulable phosphor sheet 15 are read out. This read-out is conducted by scanning the stimulable phosphor sheet 15 in the width direction thereof (main scanning direction) with the laser beam 18 emitted from the laser source 17 and deflected by the light deflector 19, and also in the length direction of the stimulable phosphor sheet 15 (sub-scanning direction) by the rotation of the stimulable phosphor sheet 15 in the direction indicated by the arrow 16, and photoelectrically detecting the light emitted from the stimulable phosphor sheet 15 by the photodetector 20 via the light transfer means 21. From the photodetector 20 is outputted an electric signal (image signal) of one X-ray projection distribution image stored in the stimulable phosphor sheet 15. The electric signal is then amplified by an amplifier 23, A/D converted by an A/D converter 24, and once stored in an image memory section 26 of a signal processing means (for example, a computer). When the read-out of one X-ray projection distribution image is finished, the portion of the stimulable phosphor sheet 15 where the read-out X-ray projection distribution image was positioned is exposed to light emitted from the erasing light source 22 to erase the radiation energy remaining in that portion of the stimulable phosphor sheet 15 after the read-out. The read-out and erasing operations are sequentially conducted for the respective X-ray projection distribution images. The image signals of the respective X-ray projection distribution images once stored in the image memory section 26 are read out and processed by the signal processing means 25 to compose a tomographic image of an arbitrary tomographic layer of the object. The composed tomographic image is displayed on an output device 27 such as a CRT.

In FIG. 1, instead of using the cylindrical stimulable phosphor sheet 15, quadrangular stimulable phosphor sheets capable of including the X-ray projection distribution images may be fitted to a cylindrical supporting frame. In this case, after the image recording is finished, the stimulable phosphor sheets may be dismounted from the supporting frame, and the respective X-ray projection distribution images may be sequentially read out separately from the respective stimulable phosphor sheets.

In the first embodiment of FIG. 1, since the X-ray projection distribution images are once stored in the stimulable phosphor sheet and then read out from the stimulable phosphor sheets, the image recording is conducted quickly without any of the time delay that occurs when there is used a two-dimensional sensor comprising many detection elements arranged two-dimensionally. Accordingly, there is no risk of the contrast and spatial resolution decreasing due to movements of the object, and it is possible to obtain a high-quality tomographic image of an arbitrary tomographic layer of the object which is free of artifacts.

Figure 2:
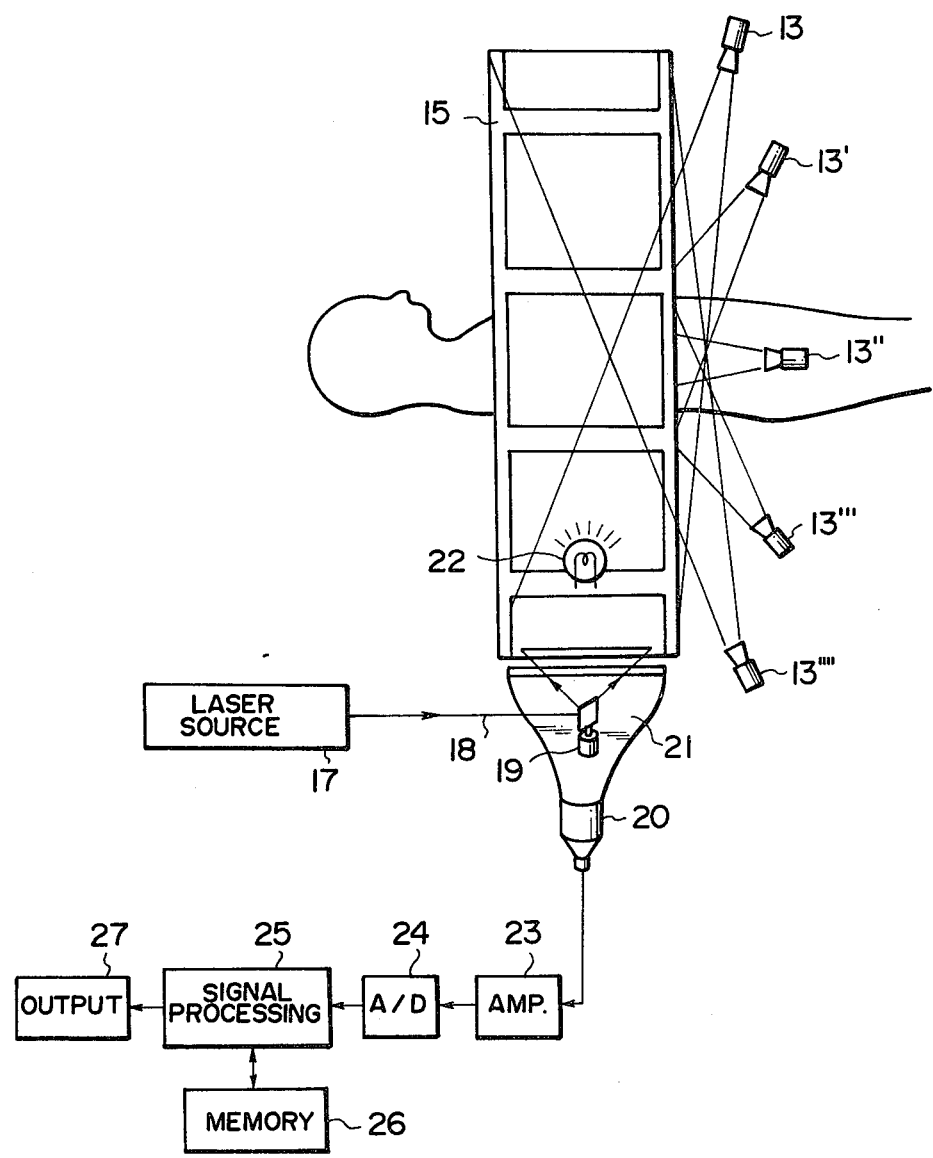
FIG. 2 is a schematic view showing a second embodiment of the apparatus in accordance with the present invention.

In FIG. 2 showing a second embodiment of the apparatus in accordance with the present invention, a plurality of X-ray tubes 13, 13', 13'', 13''' and 13'''' are positioned to obtain X-ray projection distribution images at angles different from one another with respect to the object by a single image recording operation. The read-out and the erasing of the X-ray projection distribution images stored in the stimulable phosphor sheet 15 can be conducted in the same manner as described in the first embodiment.

In the second embodiment of FIG. 2, since the X-ray projection distribution images at angles different from one another with respect to the object can be obtained by a single X-ray exposure operation, the image recording can be conducted more quickly than the first embodiment. The second embodiment is very advantageous in that a tomographic image of an arbitrary tomographic layer of the object which contains no artifact can be obtained, and an image of the organ, for example the heart, can be obtained as a still image.

In the first and second embodiments of the present invention described above, the stimulable phosphor sheet 15 is formed into a cylindrical shape. However, the stimulable phosphor sheet 15 may be formed into a quadrangular prism shape.

Figure 3A:
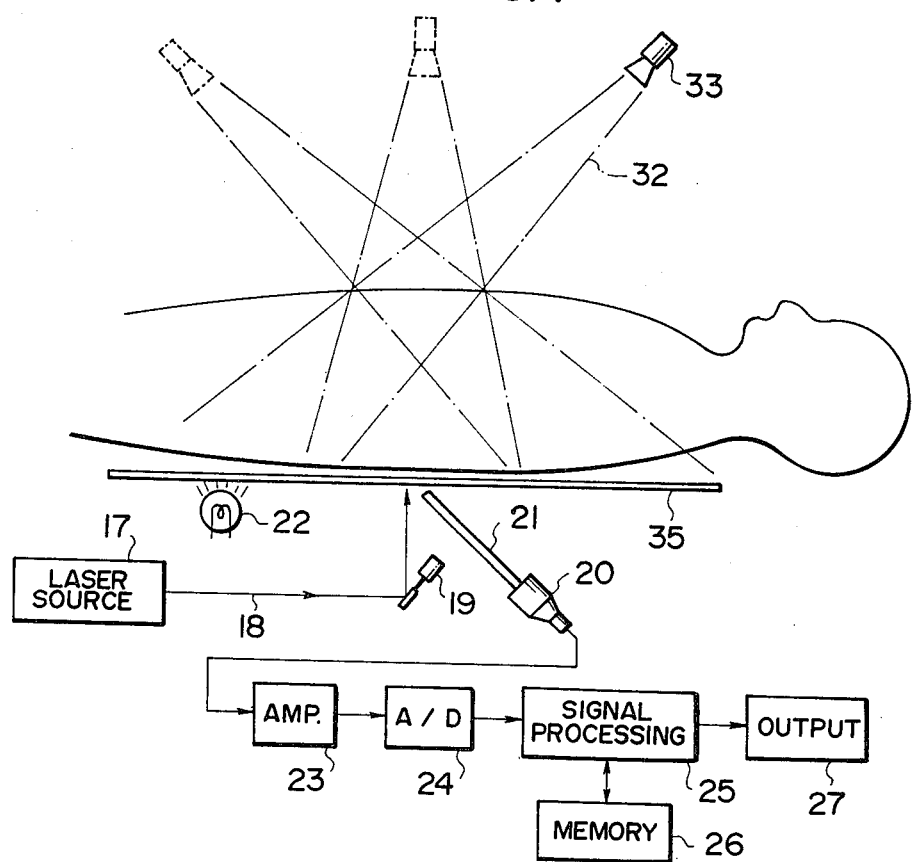
FIGS. 3A and 3B are a side view and a top view respectively showing a third embodiment of the apparatus in accordance with the present invention.
Figure 3B:
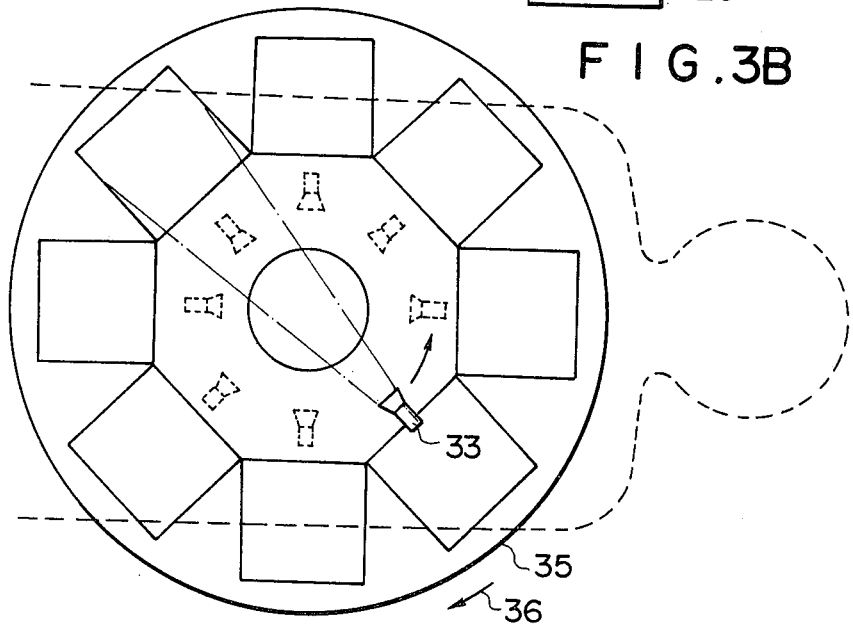

FIGS. 3A and 3B are a side view and a top view respectively showing a third embodiment of the apparatus in accordance with the present invention. In the third embodiment, a circular disk-like stimulable phosphor sheet 35 is rotatably installed. An X-ray tube 33 is positioned for rotation around a center axis to obtain X-ray projection distribution images of the object different from one another. Below the stimulable phosphor sheet 35 are positioned an optical scanning system for scanning the stimulable phosphor sheet 35 with stimulating rays, a light detecting means for photoelectrically detecting the light emitted from the stimulable phosphor sheet 35 when it is exposed to the stimulating rays, and an erasing light source 22 for releasing the radiation energy remaining in the stimulable phosphor sheet 35 after the read-out step. The optical scanning system, the light detecting means, and the erasing light source may be of the same types as those employed in the first embodiment.

In the third embodiment, image recording is conducted as described below. The X-ray tube 33 is positioned at an angle with respect to the object, and X-rays 32 are emitted pulse-wise from the X-ray tube 33. The X-rays 32 passing through the object are stored in the stimulable phosphor sheet 35 as a two-dimensional X-ray projection distribution image. After the image recording is finished at one angle with respect to the object, the X-ray tube 33 is rotated by a predetermined angle with respect to the object. The image recording is again conducted as described above to obtain another X-ray projection distribution image, which is then stored in the stimulable phosphor sheet 35 so as not to overlap the previously stored X-ray projection distribution image. The image recording mentioned above is repeated to obtain X-ray projection distribution images at equal angular intervals with respect to the object. In this manner, the image recording for obtaining a three-dimensional image of the object or an arbitrary tomographic image of the object is finished when the X-ray tube 33 has been rotated one turn (360°) around the object. After the image recording is over, the X-ray projection distribution images stored in the stimulable phosphor sheet 35 are read out. This read-out is conducted by scanning the stimulable phosphor sheet 35 in the diameter direction thereof (main scanning direction) with the laser beam 18 emitted from the laser source 17 and deflected by the light deflector 19, and also in the length direction of the stimulable phosphor sheet 35 (sub-scanning direction) by the rotation of the stimulable phosphor sheet 35 in the direction indicated by the arrow 36, and photoelectrically detecting the light emitted from the stimulable phosphor sheet 35 by the photodetector 20 via the light transfer means 21. From the photodetector 20 is outputted an electric signal (image signal) of one X-ray projection distribution image stored in the stimulable phosphor sheet 35. The electric signal is then amplified by an amplifier 23, A/D converted by an A/D converter 24, and once stored in an image memory section 26 of a signal processing means (for example, a computer). When the read-out of one X-ray projection distribution image is finished, the portion of the stimulable phosphor sheet 35 where the read-out X-ray projection distribution image was positioned is exposed to light emitted from the erasing light source 22 to erase the radiation energy remaining in that portion of the stimulable phosphor sheet 35 after the read-out. The read-out and erasing operations are sequentially conducted for the respective X-ray projection distribution images. The image signals of the respective X-ray projection distribution images once stored in the image memory section 26 are read out and processed by the signal processing means 25 to compose a tomographic image of an arbitrary tomographic layer of the object. The composed tomographic image is displayed on an output device 27 such as a CRT.

In the third embodiment, instead of using the disk-like stimulable phosphor sheet 35, quadrangular stimulable phosphor sheets capable of including the X-ray projection distribution images may be fitted to a disk-like supporting frame. In this case, after the image recording is finished, the stimulable phosphor sheets may be dismounted from the supporting frame, and the respective X-ray projection distribution images may be sequentially read out separately from the respective stimulable phosphor sheets. Further, a plurality of X-ray tubes may be used to obtain X-ray projection distribution images at angles different from one another with respect to the object by a single X-ray exposure operation.

Figure 4A:
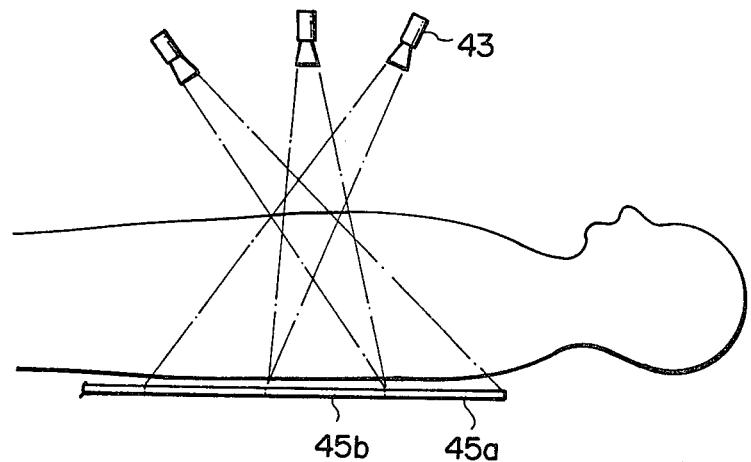
FIGS. 4A and 4B are a side view and a top view respectively showing a fourth embodiment of the apparatus in accordance with the present invention.
Figure 4B:
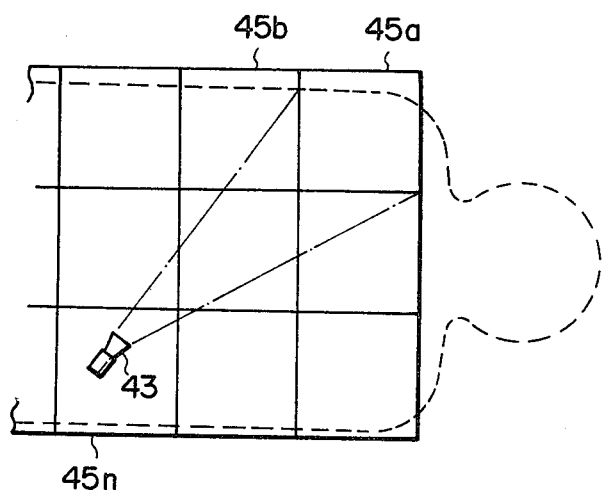

FIGS. 4A and 4B are a side view and a top view respectively showing a fourth embodiment of the apparatus in accordance with the present invention. In the fourth embodiment, stimulable phosphor sheets 45a, 45b, ..., 45n are closely positioned, and an X-ray tube 43 is positioned for rotation around a center axis to obtain X-ray projection distribution images at angles different from one another with respect to the object.

In the fourth embodiment, X-ray projection distribution images at angles different from one another with respect to the object are stored in the stimulable phosphor sheets 45a, 45b, ..., 45n while the X-ray tube 43 is moved. Then, the stimulable phosphor sheets 45a, 45b, ..., 45n carrying the X-ray projection distribution images at angles different from one another with respect to the object stored therein are separately scanned with stimulating rays to read out the stored images. From the read-out X-ray projection distribution images, a tomographic image of an arbitrary tomographic layer of the object or a three-dimensional image of the object is composed. Also in this fourth embodiment, a plurality of X-ray tubes may be used to obtain X-ray projection distribution images at angles different from one another with respect to the object by a single X-ray exposure operation.

We claim:

1. An arbitrary layer tomographic method which comprises once storing a plurality of two-dimensional X-ray projection distribution images, which are obtained by exposing an object to X-rays in a plurality of different directions, in positions different from one another in a single stimulable phosphor sheet or respectively in a plurality of stimulable phosphor sheets, scanning said stimulable phosphor sheet or sheets with stimulating rays, photoelectrically reading out the light emitted thereby from said stimulable phosphor sheet or sheets and obtaining electric signals representing the image information of a plurality of said X-ray projection distribution images, processing said electric signals and obtaining the image information representing a tomographic image of an arbitrary tomographic layer of said object.

2. A method as defined in claim 1 wherein said storing of said X-ray projection distribution images is conducted by positioning said object in the center of said stimulable phosphor sheet or sheets formed into a cylindrical shape or a polygonal prism shape, exposing said object to X-rays in a plurality of different directions and projecting a plurality of X-ray projection distribution images on said stimulable phosphor sheet or sheets formed into the cylindrical shape or the polygonal prism shape.

3. A method as defined in claim 1 wherein said storing of said X-ray projection distribution images is conducted by positioning said object above said stimulable phosphor sheet or sheets positioned in a flat form, exposing said object to X-rays in a plurality of different directions and projecting a plurality of X-ray projection distribution images on said stimulable phosphor sheet or sheets positioned in the flat form.

4. A method as defined in claim 3 wherein said stimulable phosphor sheet or sheets positioned in the flat form is in the circular disk-like form.

5. An arbitrary layer tomographic apparatus comprising an X-ray source capable of emitting X-rays in a plurality of different directions with respect to an object, at least one stimulable phosphor sheet for receiving the X-rays passing through said object and storing therein two-dimensional X-ray projection distribution images in a plurality of different directions, a scanning means for two-dimensionally scanning said stimulable phosphor sheet with stimulating rays, a photoelectric converting means for photoelectrically reading out the light emitted from said stimulable phosphor sheet by said scanning with stimulating rays and obtaining image signals, and a signal processing means for composing a tomographic image of an arbitrary tomographic layer of said object from said image signals.

6. An apparatus as defined in claim 5 wherein said X-ray source comprises a single X-ray tube, which is ratatable around said object.

7. An apparatus as defined in claim 5 wherein said X-ray source comprises a plurality of X-ray tubes which can simultaneously emit X-rays in a plurality of different directions with respect to said object.

8. An apparatus as defined in any of claims 5 to 7 wherein said at least one stimulable phosphor sheet is formed into a cylindrical shape or a polygonal prism shape so as to include said object in the center.

9. An apparatus as defined in any of claims 5 to 7 wherein said at least one stimulable phosphor sheet is positioned in a flat form on the side opposite to said X-ray source with respect to said object.

10. An apparatus as defined in claim 9 wherein said at least one stimulable phosphor sheet positioned in the flat form is in the circular disk-like form.

* * * * *